(12) United States Patent
Duncan (10) Patent No.: US 9,500,287 B2
(45) Date of Patent: Nov. 22, 2016

(54) VALVE WITH POSITIVE AND NEGATIVE STATUS INDICATOR

(71) Applicant: David R. Duncan, Penryn, CA (US)

(72) Inventor: David R. Duncan, Penryn, CA (US)

( * ) Notice: Subject to any disclaimer, the term of this patent is extended or adjusted under 35 U.S.C. 154(b) by 195 days.

(21) Appl. No.: 14/539,075

(22) Filed: Nov. 12, 2014

(65) Prior Publication Data
US 2015/0129061 A1    May 14, 2015

Related U.S. Application Data

(60) Provisional application No. 61/904,080, filed on Nov. 14, 2013.

(51) Int. Cl.
*F16K 11/085* (2006.01)
*F16K 37/00* (2006.01)

(52) U.S. Cl.
CPC ....... *F16K 11/0853* (2013.01); *F16K 37/0058* (2013.01); *Y10T 137/8225* (2015.04)

(58) Field of Classification Search
CPC .................................... F16K 11/0853
USPC ......... 137/625.46, 625.47, 553, 556; 40/331, 40/332; 604/167.05; 116/277, 298
See application file for complete search history.

(56) References Cited

U.S. PATENT DOCUMENTS

| | | | | |
|---|---|---|---|---|
| 1,427,239 | A * | 8/1922 | Spencer | B60R 25/04 137/552.5 |
| 1,985,449 | A * | 12/1934 | Heggem | F16K 5/184 116/277 |
| 3,238,968 | A * | 3/1966 | Pecis | F16K 11/078 116/277 |
| RE26,838 | E * | 3/1970 | Pecis | F16K 31/60 116/277 |
| 3,834,372 | A * | 9/1974 | Turney | A61B 5/0215 137/625.47 |
| 3,957,082 | A * | 5/1976 | Fuson | A61M 5/1408 128/DIG. 26 |
| 4,219,021 | A | 8/1980 | Fink | |
| 4,470,429 | A * | 9/1984 | Johnson | F16K 11/0853 137/270 |
| 4,494,565 | A | 1/1985 | Sinclair | |
| 4,566,480 | A | 1/1986 | Parham | |
| 4,593,717 | A * | 6/1986 | Levasseur | F16K 11/085 137/556.6 |
| 4,950,230 | A * | 8/1990 | Kendell | A61M 1/28 137/625.41 |
| 5,046,528 | A * | 9/1991 | Manska | F16K 31/602 137/385 |
| 5,074,334 | A | 12/1991 | Onodera | |
| 5,144,972 | A | 9/1992 | Dryden | |
| 5,156,186 | A | 10/1992 | Manska | |
| 5,466,228 | A * | 11/1995 | Evans | F16K 11/0853 137/625.47 |
| 5,605,176 | A | 2/1997 | Herzberger | |
| 6,076,554 | A * | 6/2000 | Jensen | F16K 11/0853 137/625.47 |
| 6,158,467 | A | 12/2000 | Loo | |
| 6,230,744 | B1 | 5/2001 | Ahrweiler | |
| 6,418,966 | B2 | 7/2002 | Loo | |
| 6,457,488 | B2 | 10/2002 | Loo | |

(Continued)

*Primary Examiner* — Craig Schneider
*Assistant Examiner* — Daniel P Donegan
(74) *Attorney, Agent, or Firm* — Heisler & Associates (57) ABSTRACT

A valve is provided with multiple ports joining multiple fluid conduits leading between fluid sources and fluid destinations. A central hub manifold or other control element resides within a body supporting the ports, and can rotate relative to the valve body. Fluid flow paths within the central hub or other control element are selectively aligned or not aligned with the ports. The valve indicates which ports are open or closed by providing unique marks adjacent the ports corresponding with being open or closed. When the positive marks are visible, such as through windows in a rotating structure fixed to the central hub or other control element, the corresponding ports are open. When the negative marks are visible, such as through other windows in the rotating structure, the corresponding ports are closed.

20 Claims, 10 Drawing Sheets

(56) References Cited

U.S. PATENT DOCUMENTS

| | | |
|---|---|---|
| 6,953,450 B2 | 10/2005 | Baldwin |
| 7,232,428 B1 | 6/2007 | Inukai |
| 7,744,573 B2 * | 6/2010 | Gordon ............... A61B 5/0215 600/584 |
| 7,984,730 B2 * | 7/2011 | Ziv ..................... A61M 39/223 137/239 |
| 8,584,701 B2 * | 11/2013 | Duncan ............... F16K 11/0853 116/277 |
| D728,745 S * | 5/2015 | Duncan ....................... D23/233 |
| 9,212,762 B2 * | 12/2015 | Duncan ............... F16K 11/0853 |
| 2004/0045613 A1 * | 3/2004 | Hinojosa, Jr. .......... A61H 33/60 137/625.47 |
| 2008/0067462 A1 * | 3/2008 | Miller ................... A61M 39/22 251/149.1 |
| 2011/0011474 A1 * | 1/2011 | Duncan ............... F16K 11/0853 137/625.47 |
| 2014/0076431 A1 * | 3/2014 | Duncan ............... F16K 11/0853 137/556.6 |
| 2015/0129061 A1 * | 5/2015 | Duncan ............... F16K 11/0853 137/553 |

* cited by examiner

VALVE WITH POSITIVE AND NEGATIVE STATUS INDICATOR

CROSS-REFERENCE TO RELATED APPLICATIONS

This application claims benefit under Title 35, United States Code §119(e) of U.S. Provisional Application No. 61/904,080 filed on Nov. 14, 2013, and incorporates by reference all of the contents of U.S. Pat. No. 8,584,701 issued on Nov. 19, 2013.

FIELD OF THE INVENTION

The following invention relates to valves for opening and closing fluid pathways. More particularly, this invention relates to valves, including stopcocks such as those used in the medical fields, for routing fluids or medication (medicament) into tubing, a device, multiple devices, a patient or any combination thereof. These valves allow for control of fluid flow between various different sources and destinations within a given system.

BACKGROUND OF THE INVENTION

In the scientific fields it is often necessary to manipulate fluid flow through conduits by opening, closing and diverting fluid flow to transport or mix various fluids from various sources. The most common example of this occurs in medicine where medicament (medication or fluid) infusing into a patient via an intravenous or central line) need to be mixed with another infusing medicament in a way that can be manipulated so as to allow or disallow the various infusions as required. These same fluid systems need to allow the practitioner direct sterile access so that a given medicine or fluid may be directly injected, pressure may be directly monitored, or body fluid may be directly removed for sampling.

A common way to accomplish this is through the use of medical stopcocks which are most commonly of the "3 way type" or less commonly "4 way type" (these stopcocks are shown in FIG. 1). These inventions allow ports to be opened or closed as need be to allow or disallow the flow of a given medicament or to allow direct access to the fluid system for the above stated reasons.

A common problem with the use of these 3 and 4 way medical stopcocks is the manipulation or setting of their flow patterns (operable or functional state) based on one's visual assessment. The user must rotate a central hub to align flow through the desired ports based on his or her ability to understand and interpret the functionality of the stopcock. This functionality is most commonly delineated by a single knob which points to the port that is closed, making interpretation of those that are open difficult. This lack of positive delineation leads to misinterpretation of flow patterns with concomitant errors in settings and associated medication errors which may lead to harm or death.

The difficulty in interpreting the flows that will be allowed from a given setting also limits the number of combinations (i.e. 4 way). This limit occurs because with stopcocks that offer more than four combinations (i.e. 4 way), interpretation and manipulation become too complicated and the chances for error increase exponentially. This limits the current technology and requires assembling two or more of the standard stopcocks in series (an arrangement known as a "manifold") if more choices are required. This increases cost, complexity and each stopcock in the chain multiplies the chance of medication errors.

RELEVANT PRIOR ART

U.S. Pat. No. 3,957,082 May 18, 1976 Fuson
U.S. Pat. No. 4,593,717 Jun. 10, 1986 Levasseur
U.S. Pat. No. 4,566,480 Jan. 28, 1986 Parham
U.S. Pat. No. 5,144,972 Sep. 8, 1992 Dryden
U.S. Pat. No. 5,156,186 Oct. 20, 1992 Manska
U.S. Pat. No. 4,219,021 Aug. 26, 1980 Fink
U.S. Pat. No. 6,158,467 Dec. 12, 2000 Loo
U.S. Pat. No. 6,230,744 May 15, 2001 Ahrweiler
U.S. Pat. No. 6,418,966 Jul. 6, 2002 Loo
U.S. Pat. No. 6,457,488 Oct. 1, 2002 Loo
U.S. Pat. No. 6,953,450 Oct. 11, 2005 Baldwin
U.S. Pat. No. 7,232,428 Jun. 19, 2007 Inukai All prior art stopcocks, including those listed above are fraught with less than adequate demarcations or indications for whether a given port is in the open or closed position. This problem yields difficulty and error in determining the functionality of the prior art stopcock at any given "setting."

Levasseur's stopcock (U.S. Pat. No. 4,593,717) demonstrates a stopcock with enhanced demarcation of the ports which are open, but does not demarcate which ports are closed, and this design offers a multitude of positions where various ones of the three ports are closed, leaving this interpretation up to the user by a "process of elimination." The port configuration, operable states and operable configurations are also not consistent with the prior art, making it less intuitive.

Manska's stopcock (U.S. Pat. No. 5,156,186) does make an attempt to better delineate whether the given port is on or off, by having the "o" in "on" or "off" traverse between the two words, thereby spelling the status of the port it overlies as "on" or "off," but also leaving remnants of words like "ff" over the other ports. This is an improvement over the prior art, but still requires reading, interpreting and assessing each port before the overall functional state can be determined. This modality does not let one interpret at a glance which ports are open and (in use) and is again associated with a greater degree of error than this invention. This modality only allows up to a "3 way" complexity secondary to these limitations.

Loo's stopcocks (U.S. Pat. Nos. 6,158,467, 6,418,966 and 6,457,488) do include a one sided central fluid path in the hub (on the knob side). This single sided central port only communicates with the outer ports, and does not allow for fluid flow all the way through the hub. Loo's stopcock functionality is very hard to interpret making it difficult to know which ports are open and which are closed. His designs include two separate non-mixing fluid paths which increases the complexity and chance for medication errors, particularly so with the lack of an adequate flow designation system. The optional central fluid flow path of the present invention offers a much needed advantage over this design and others, allowing fluid from an IV or other source to flow through the central hub, independent of the hubs rotated position with respect to the fluid conveyance ports (as is required by the Loo designs), thereby increasing overall functionality, useful ports, and ease in interpreting the functional state. This invention, for instance, could allow fluid to continue flowing through the central port while all other ports were off (Loo's design has no means to accomplish this). Loo's designs only allow flow from the central port to the peripheral ports.

Other types of valves, including irrigation two-way ball valves can be misinterpreted by users, especially those with limited experience using such valves. Thus, a clearer status indicator on the valve would improve the usefulness of the valve and decrease the propensity for error.

SUMMARY OF THE INVENTION

With this invention a valve is provided which can be both easily manipulated to produce the flow desired between separate ports as well as be readily analyzed to determine the current functional or operational state of the valve and relative flow therethrough at a glance. The valve generally includes a valve body with multiple fluid pathways, such as fluid conveyance ports, joined to the valve body. A central hub defines a preferred form of central manifold which resides within the valve body. This central hub can be rotated within the valve body. Fluid flow paths embedded within the central hub allow for fluid flow therethrough. By aligning ends of the fluid flow paths with the fluid conveyance ports in different orientations, various different ones of the ports are caused to be open or closed to allow or block fluid flow into and out of the valve. This central hub can also be in the form of a standard ball within a typical two-way ball valve such as that used in irrigation or some other specific type of valve.

Uniquely with this invention, a pair of indicator portions are provided including a first indicator portion and a second indicator portion relating to valve operational status. These first and second indicator portions interact with each other to provide this operational status information. One of the indicator portions includes positive markings generally aligned with the fluid conveyance ports joined to the valve body and negative markings also aligned with the ports. The second indicator portion includes a visual barrier which is coupled to the central hub so that the second indicator portion rotates with the central hub. This visual barrier is configured to block markings of the first indicator which are incorrect and not block markings on the first indicator which correspond with ports which are open and closed. In a preferred form of this invention, the second indicator portion is in the form of a plate with windows therein. Positive windows are generally aligned with the ends of the fluid flow paths in the central hub and negative windows are spaced between these fluid flow paths in the central hub. Thus, when these ends of the flow paths of the central hub are aligned with the ports, the positive windows in the rotating plate are aligned with the positive markings of the first indicator portion, so that the positive markings can be seen by a user. The user sees a positive marking adjacent each port which is open. Also, negative windows are aligned with the negative markings of the first indicator portion so that the user sees a negative marking next to each port which is closed. The user can thus readily determine which ports are open and which ports are closed and hence which ports are delivering or receiving fluid within the system in which the valve is located.

Various different numbers of ports can be associated with the valve body. Also, various different numbers of ends of fluid paths can be provided along with the central hub. By altering the number of ports associated with the valve body and altering the positions of ends of the flow paths within the central hub, various different numbers of operational states for the stopcock can be provided.

The central hub can optionally include a "flow through" central fluid path preferably extending substantially axially and perpendicular to and/or through the embedded flow paths within the central hub and perpendicular to the ports extending from the valve body. This central fluid conveyance path allows fluid to flow all the way through the center of the hub and is connected with the embedded fluid flow paths which are located within the central hub.

This central fluid conveyance path functions as a distinct flow through fluid route that connects with the open fluid conveyance ports via the connected flow paths within the central hub. This central path adds additional functionality by allowing fluid flow through the center of the valve without using the fluid conveyance ports for this purpose, thereby sparing them for other uses. The central fluid conveyance path is not opened or closed by rotation of a central hub as are the ports joined to the valve body. Rather, this central path always allows for continuous fluid flow through it, while rotation of the central hub determines which of the fluid conveyance ports joined to the valve body will be connected to the central flow path. With such a central fluid conveyance path, valves may offer additional functionality with minimal increased complexity. This central fluid path design allows for more complicated valves with increased functionality, while minimizing cost and confusion. A typical appearing four way stopcock type valve with a central fluid path could be easily designed to accommodate eight combinations, whereas to obtain eight combinations previously would have required three prior art stopcocks to be connected in series as a "manifold" of stopcocks. The first and second indicator portions mentioned above would also be present in a preferred embodiment of stopcocks containing a central fluid path.

This disclosure also incorporates by reference the contents of U.S. Pat. No. 8,584,701 in its entirety.

OBJECTS OF THE INVENTION

Accordingly, a primary object of the present invention is to provide a rapid means of assessing the functional status of a valve and its attachments.

Another object of the present invention is to provide a valve which can be both readily assessed as to its setting status while still being used in a manner familiar to those already trained in the use of prior art valves.

Another object of the present invention is to provide a stopcock type valve which can be simply assessed as to its functional and operational status to minimize the opportunity for errors in utilizing the stopcock, including medication errors.

Another object of the present invention is to provide a valve with an intuitive operational status designating system.

Another object of the present invention is to provide a valve which allows multiple different fluid flow combinations while still maintaining ease of use and safety.

Another object of the present invention is to provide a valve which can replace multiple separate valves arrayed in a manifold, to simplify complex fluid flow arrangement systems.

Another object of the present invention is to provide a valve which can be readily interpreted as to its operational state, by providing both positive and negative markings as to the valve state.

Another object of the present invention is to provide a valve which can be of simple manufacture and formed of low cost materials, such as by utilization of injection molded plastics.

Another object of the present invention is to provide an indicator for indicating a status of the valve which can be configured at various different positions on the stopcock for high visibility in various different fluid flow systems in which the valve is included.

Other further objects of the present invention will become apparent from a careful reading of the included drawing figures, the claims and detailed description of the invention.

DETAILED DESCRIPTION OF THE PREFERRED EMBODIMENT

Referring to the drawings, wherein like reference numerals represent corresponding related parts throughout the various drawing figures, reference numeral 1 is directed to a prior art stopcock type valve (FIGS. 1-5). This prior art stopcock 1, as well as the various stopcocks 20, 30, 40, 50, 110 of this invention (FIGS. 6-44) and other specific valve embodiments 130, 140 (FIGS. 45-48) share many common attributes, as well as important distinctions, elucidated herein through reference to exemplary embodiments depicted herein. This invention is also related to U.S. Pat. No. 8,584,701, incorporated herein by reference in its entirety. Through manipulation of these valves, various different fluid conveyance ports 4 joined to a valve body 2 can be either opened or closed for fluid flow therethrough, such as indicated by flow arrows on the drawings associated with the different embodiments. For each embodiment, different views are provided to show the various different positions of a central hub 12 relative to the valve body 2, as well as relative positions of a fixed plate 6 relative to a rotating plate 18, 21, 31, 41, 51, 111, 131, 141 or other structure which quickly and easily indicates which of the fluid conveyance ports 4 are open through the valve.

With particular reference to FIGS. 1-9, basic details common to both prior art stopcocks 1 and the stopcocks 20, 30, 40, 50, 110 of this invention are described. A valve body 2 acts as a housing containing a central hub 12 therein. This valve body 2 has a substantially cylindrical recess. A central hub 12 having a substantially cylindrical form matching that of this recess resides in the recess within the valve body 2. The valve body 2 and central hub 12 can be fitted with seals or manufactured with sufficiently tight tolerances and from appropriate materials to be substantially self-sealing.

The valve body 2 includes a plurality of fluid conveyance ports 4 extending radially from the valve body 2. Each of these ports 4 ends at a terminus 3 most distant from the valve body 2. The terminus 3 of each port 4 typically is configured so that it can be coupled to other fluid conduits, such as medical tubing or directly to sources or destinations of fluids within the system. These sources or destinations can include sensors, medication vials, syringes, a patient interface (e.g. an intravenous catheter), an infusion pump or other fluid handling or processing equipment. The connectors utilized at the terminii 3 can be luer fittings, screw fittings or other forms of fittings common for tubular connectors, including sleeve and clamp connectors and press fit connectors. Ports 4 which are open are identified with the reference numeral 10.

Figure 18:
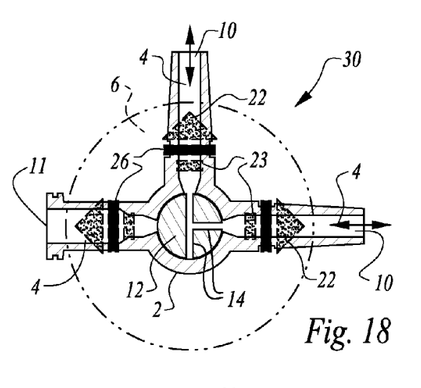
FIGS. 18-23 are top plan views and sectional views of a three way stopcock in various functional states according to this invention.
Figure 19:
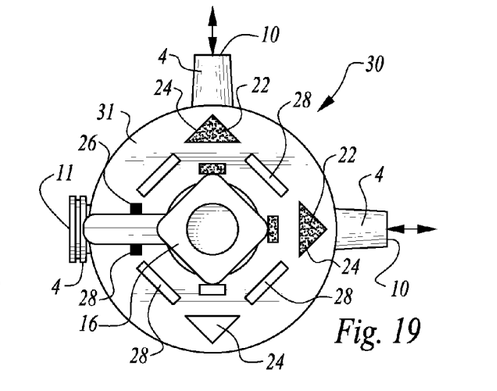
Figure 20:
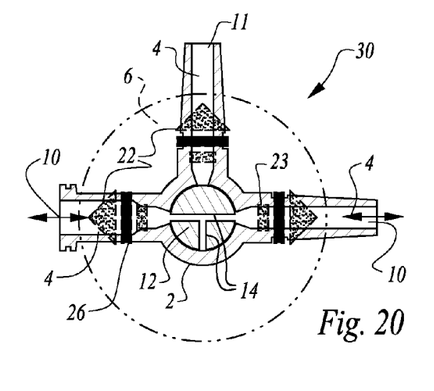
Figure 21:
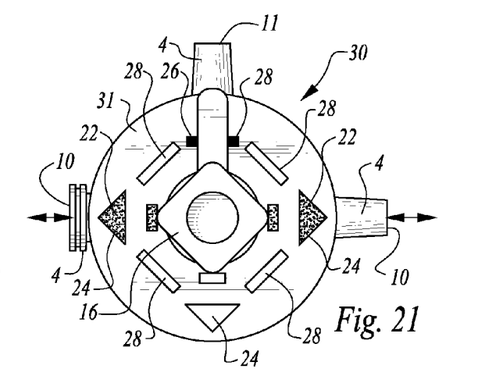
Figure 22:
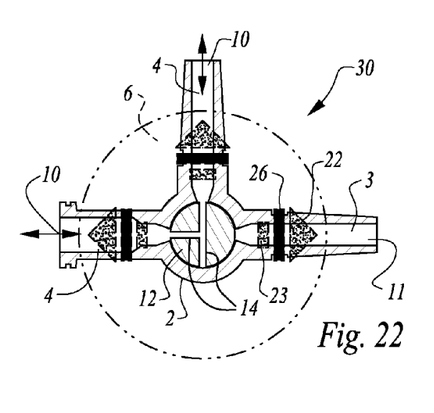
Figure 23:
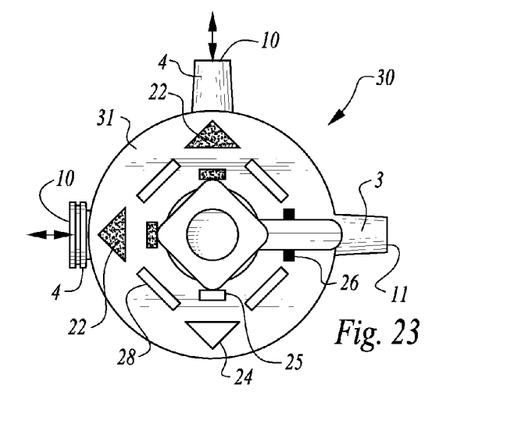
Figure 24:
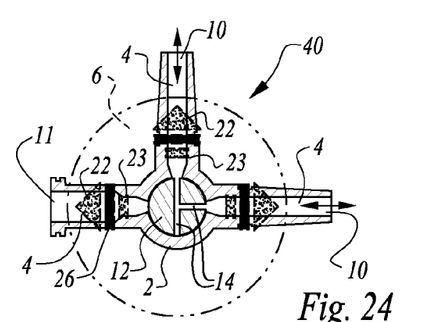
FIGS. 24-31 are top plan views and full sectional views of a four way stopcock in various functional states according to this invention.
Figure 25:
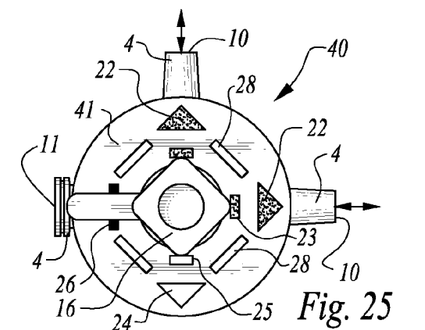
Figure 26:
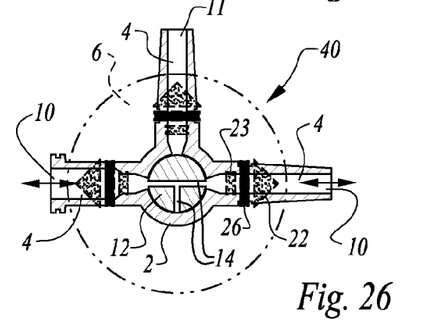
Figure 27:
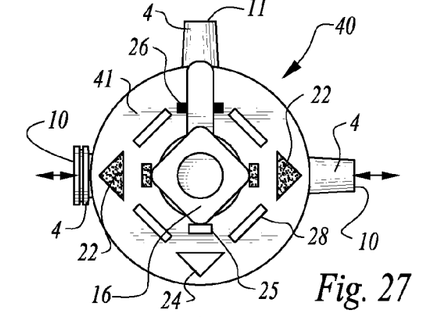
Figure 28:
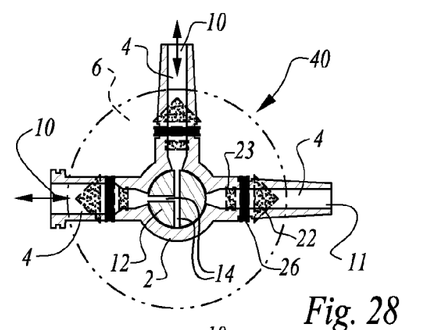
Figure 29:
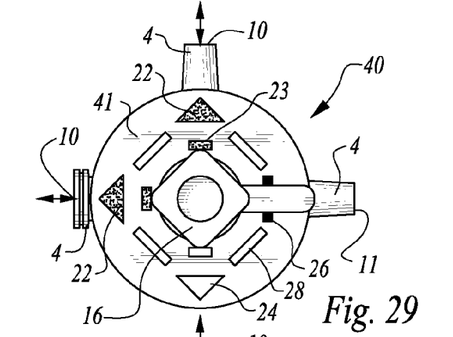

Ports 4 which are closed are provided with the reference numeral 11. Furthermore, open ports are provided with arrows indicative of fluid flow potential through the stopcock 1 (FIGS. 1-45). A central fluid conveyance path 9 (FIGS. 9 and 13) can optionally be provided through the central hub 12. This central fluid conveyance path 9 intersects embedded fluid flow paths 14 within the central hub 12 (FIGS. 18, 20 and 22).

Typically, this central hub 12 is formed along with a central control knob 16 or is configured so that the central control knob 16 can be attached thereto. A pin connector 17 can accommodate such attachment when the knob 16 is on a rear of the valve body 2 (FIGS. 10-13). The embedded flow paths 14 can be formed by drilling or through other forming techniques, such as part of the injection molding process.

To provide the indication of functional state of operation of the stopcock 30 according to a preferred embodiment of this invention (FIGS. 6-13) a pair of plates are provided as indicator portions, including a fixed plate 6 and a rotating plate 18. The fixed plate 6 is fixed relative to the valve body 2 and fluid conveyance ports 4. This fixed plate 6 includes various markings including positive markings 22, 23 generally aligned with the fluid conveyance ports 4 and negative markings 26 also presented for selective display. The rotating plate 18 is configured to block the fixed plate 6 and its markings except where windows 24, 25, 28 in the plate 18 properly indicate valve operational status: when positive markings 22, 23 are aligned with the positive windows 24, 25 which are aligned with embedded fluid flow paths 14 within the central hub 12, and when negative markings 26 are aligned with negative windows 28 spaced away from the paths 14. At these locations, the windows 24, 25, 28 are formed in the rotating plate 18 that allow the underlying markings 22, 23, 26 on the fixed plate 6 to be revealed or viewed through appropriate ones of the windows 25, 26, 28. In particular, the radial distances from the central rotational axis of the rotating plate 18 and the center point of the fixed plate 6 match for the windows 24 and the markings 22, for the windows 25 and the markings 23, and for the windows 28 and the markings 26.

The rotating plate 18 rotates with the central hub 12 so that the positive windows 24, 25 always remain aligned with the embedded fluid flow paths 14 within the central hub 12, and the negative windows 28 remain spaced from the paths 14. When the embedded fluid flow paths 14 are aligned with the fluid conveyance ports 4 in the valve body 2, the positive windows 24, 25 are automatically aligned with the positive markings 22, 23 on the fixed plate 6, so that these markings can be seen through the positive windows 24, 25. When the paths 14 are out of alignment with the ports 4, the negative windows 28 are aligned with the negative markings 26. By placing the positive markings 22, 23 and the negative markings 26 differing radial distances from a rotational axis of the hub 12, and providing the positive windows 24, 25 and the negative windows 28 a similar radial distance from the rotational axis, the positive markings 22, 23 are always covered when the negative markings 26 are revealed and vice versa. These markings can be formed of bright colors or glow in the dark type materials to further enhance the ability of a user to readily see the operable state of the stopcock 30 (FIGS. 6-13) and thus which ports 4 are currently open and which ports 4 are closed. For instance, the positive markings can be green (depicted with stipple shading in the figures) and the negative markings can be red (depicted by solid shading in the figures).

Figure 1:
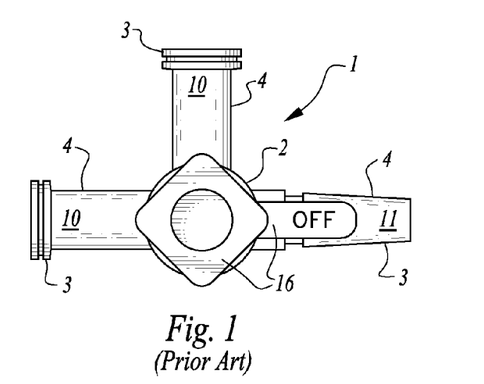
FIG. 1 is a top plan view of a standard prior art stopcock type valve.
Figure 2:
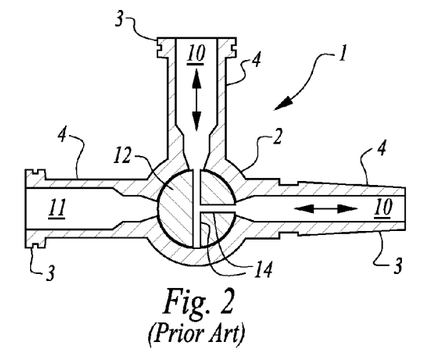
FIGS. 2-5 are full sectional views similar to that which is shown in FIG. 1 and illustrating four different orientations for a central hub of the prior art stopcock, with arrows indicating which ports of the stopcock are open for fluid flow therethrough.
Figure 3:
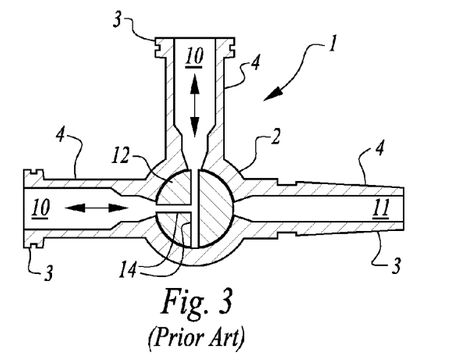
Figure 4:
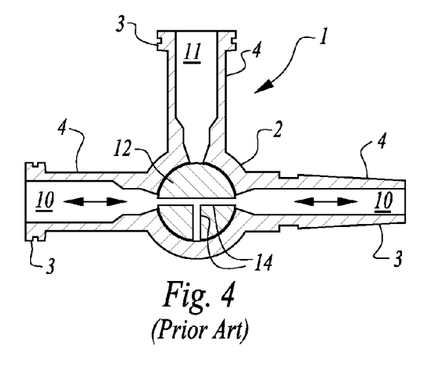
Figure 5:
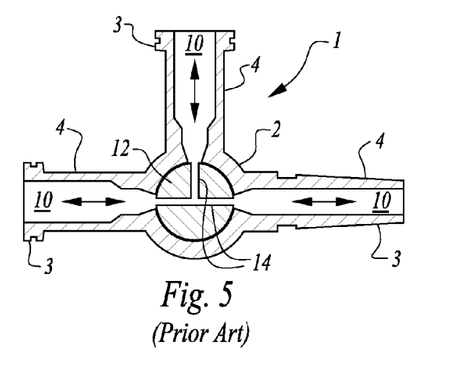
Figure 6:
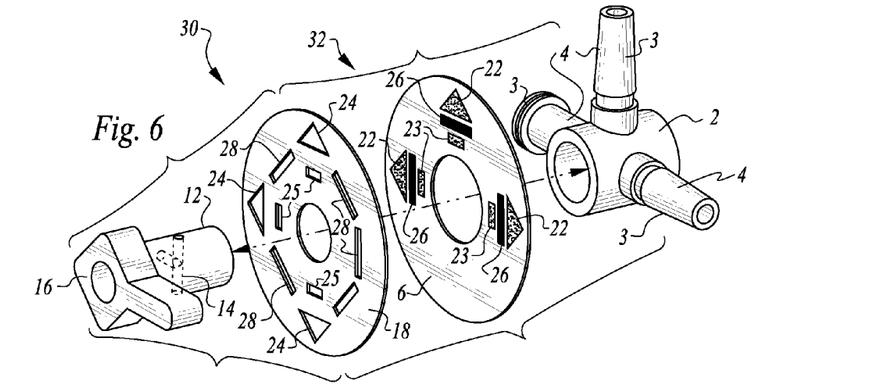
FIGS. 6 and 7 are perspective views of a three or four way stopcock valve according to this invention, with FIG. 6 fully exploded and FIG. 7 partially exploded, and showing how the two indicator plates work together to provide both positive and negative indicators of valve port status.
Figures 7, 8, 9:
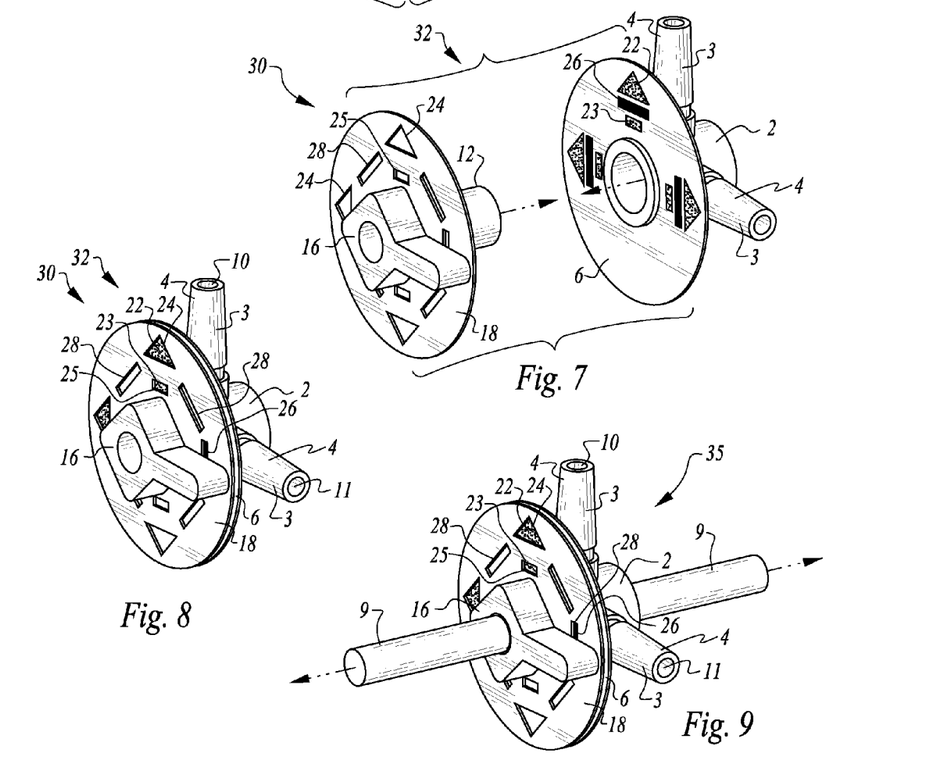
FIG. 8 is a perspective view of that which is shown in FIGS. 6 and 7 with the stopcock shown fully assembled.
FIG. 9 is a perspective view of an alternative of the stopcock shown in FIGS. 6-8 that additionally includes a central fluid conveyance path extending axially along a rotational axis thereof.
Figures 10, 11, 12, 13:
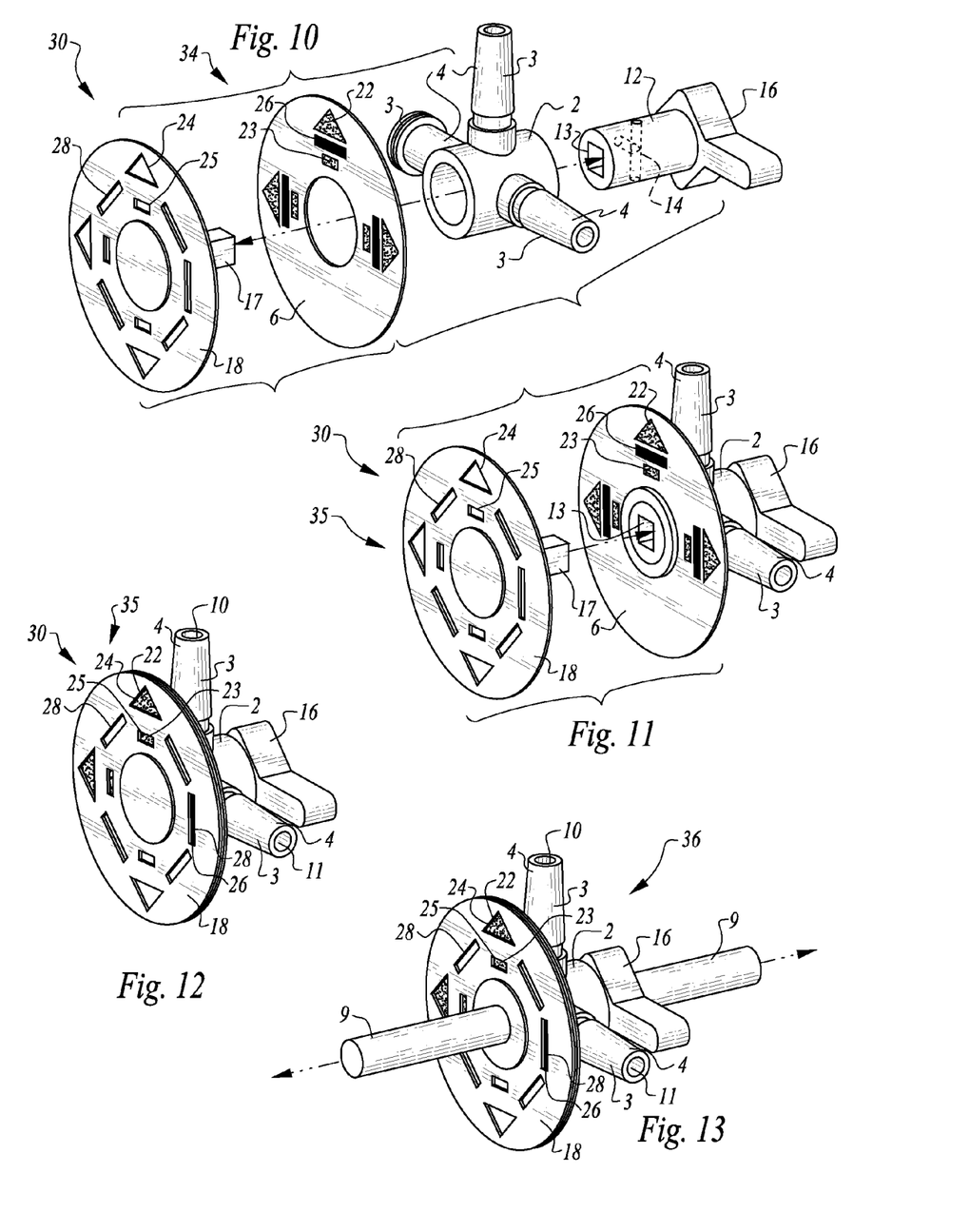
FIGS. 10-13 correspond with FIGS. 6-9 except depicting how two indicator plates of the stopcock can be positioned on a side of the stopcock opposite a central control knob as opposed to on the same of the central control knob.
Figure 14:
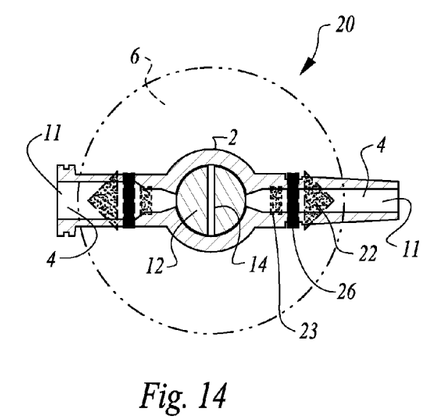
FIGS. 14-17 are top plan views and sectional views of a two way stopcock in various functional states according to this invention.
Figure 15:
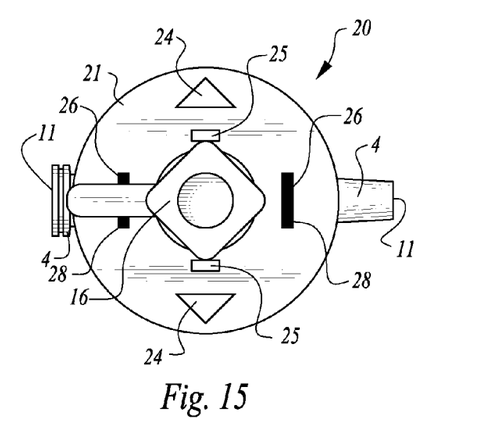
Figure 16:
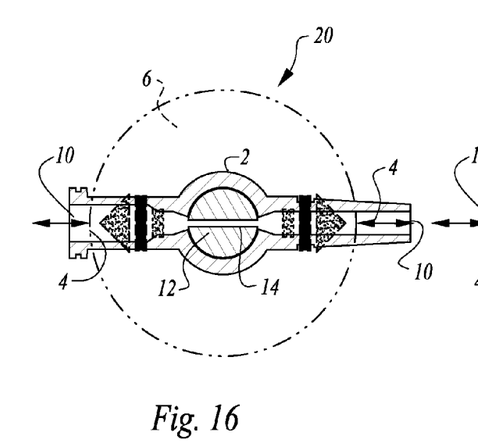
Figure 17:
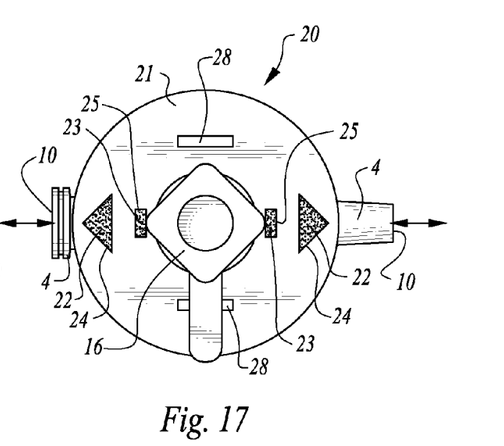

With such a configuration, the stopcock 30 works in a fashion consistent with prior art stopcocks 1, but with clear indicators both positively identifying open ports 4 and negatively identifying closed ports 4, thereby minimizing confusion or misuse. The use involves rotation of the central control knob 16, which rotates the central hub 12 to create open fluid connections between the fluid conveyance ports 4. The additional placement of the rotating plate 18 fixed to the central hub 12, and overlying the fixed port identification markings adds the additional clear demarcation of the status of the ports 4 as visualized through the windows 24, 25, 28. The plates 6, 18 can be on either side of the ports 4, as shown in FIGS. 8 and 12. Alternatively, two sets of plates 6, 18 could be provided one on each side of the stopcock 30. Also, two knobs 16, one on each side, could be provided. Although not shown, a fixed gripping area on the stopcock side opposite the knob 16 could also be placed to allow the user's opposite hand to hold the stopcock while the primary hand turns the knob. Such gripping area could be a high friction material on the surface or ribs, bands, plates, etc. that facilitate enhanced gripping.

As rotation of the central hub 12 causes the windows 24, 25, 28 to be aligned with the markings 22, 23, 26, rotation of the central hub 12 also brings the embedded fluid flow paths 14 contained therein into alignment with a desired fluid conveyance ports 4 attached to the periphery of the valve body 2. Thus, the desired open port 10 and closed port 11 configuration determined by the central hub 12 position is created relative to the valve body 2 and its fluid conveyance ports 4.

Optionally, detents can be provided between the central hub 12 and the valve body 2, such as every 30°, 45° or 90° of central hub 12 rotation, or whenever flow paths 14 have ends thereof aligned with ports 4 in the valve body 2, to improve accuracy of positioning of the central hub 12 relative to the valve body 2. Such detents could be formed as teeth and slots formed in the central hub 12 and the recess in the valve body 2 or in other ways consistent with the prior art. Such detents are particularly desirable when more complex stopcock combinations are used.

With particular reference to FIGS. 14-17, details of a two way stopcock 20 are described. This two way stopcock benefits from use of the indicator disks 6, 21, in a simplest stopcock of a two way variety 20. Only when the embedded fluid flow paths 14 are aligned with the ports 4 are the marks aligned with the appropriate windows to indicate that fluid flow can occur (FIGS. 16 and 17) through the two way stopcock 20. Otherwise, the positive marks 22, 23 are blocked by the plate 21 (FIGS. 14 and 15) and the negative marks 26 are revealed while in this "off" position.

With particular reference to FIGS. 18-23, details of a three way stopcock 30 are described. With this three way stopcock 30, three ports 4 are provided as shown (note that in all the figures, it is assumed that various different type connector ends (terminiis may be present in various configurations), with two of the ports 180° spaced from each other and one of the ports 90° spaced from each of the other two ports. Correspondingly, fluid flow paths 14 have three ends spaced 90° from each other in a pattern matching that of the ports 4. In this three way stopcock 30, a central hub 12 is only able to rotate 180°. The three "open flow" operable positions (any two ports open) for this central hub 12 relative to the valve body 2 are depicted, with the marks indicating which ports 4 are open (or closed) by the marks being visible through the windows in the plate 31. This enhanced demarcation system also allows additional operable positions in-between those shown where all three ports are closed, thereby offering additional safety compared to the prior art.

Figure 30:
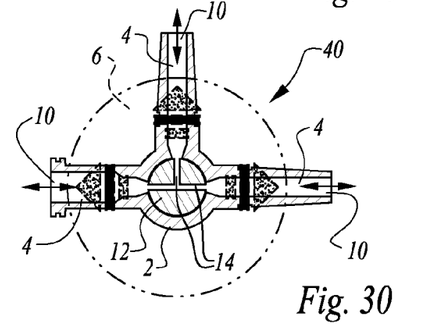
Figure 31:
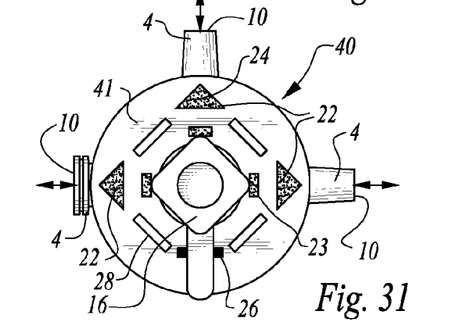

With particular reference to FIGS. 24-31, details of a four way stopcock 40 are described. The four way stopcock 40 is similar in configuration to the three way stopcock 30. However, the central hub 12 is allowed to rotate 360°. Thus, a three way flow option (as depicted in FIGS. 30 and 31) is facilitated with the four way stopcock 40 of FIGS. 24-31. The plate 41 with windows thereon is similar to the plate 31 of the previous embodiment. By allowing the central hub 12 and associated embedded flow paths 14 to rotate 360° relative to the valve body 2 and associated fluid conveyance ports 4, a position is facilitated where all three fluid conveyance ports 4 are open to each other simultaneously, as well as the positions described above with respect to the three way stopcock 30 of FIGS. 18-23. Like the three way stopcock above, this four way stopcock allows intermediate positions where all ports may be closed.

With particular reference to FIGS. 32-43, details of a six way stopcock 50 are described according to a first embodiment. With the six way stopcock 50, four fluid conveyance ports 4 are associated with the six way stopcock 50. These four ports 4 are each spaced a similar distance apart from each other, and in a common plane, such that they are substantially 90° from adjacent ports 4. The central hub 12 is configured to include embedded fluid flow paths 14 in a particular configuration to allow for selective opening and closing of the various ports 4 in at least six different configurations.

In particular, the flow paths 14 of this preferred embodiment of the six way stopcock 50, the fluid flow paths 14 follow a pattern somewhat similar to the capital letter "K." However, several other flow path design configurations are possible. Such as those in co-pending U.S. Pat. No. 8,584, 701, incorporated herein by reference. Four ends are provided for the flow paths 14 and the flow paths are all joined together centrally within the central hub 12. These four ends of the flow paths 14 are at the end of flow path segments that radiate from a center of the central hub 12. Two of these flow path segments are 180° opposite each other. Two additional flow path segments are 90° spaced from each other and 45° spaced from the flow path segments that are oriented 180° away from each other.

Figure 32:
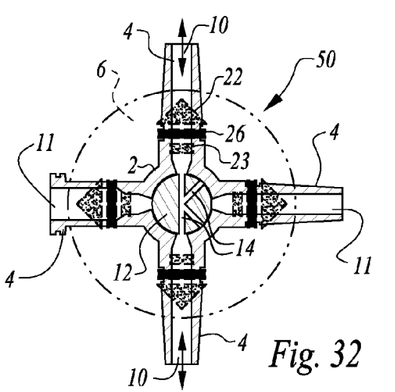
FIGS. 32-43 are top plan views and full sectional views of a six way stopcock in various functional states according to this invention.
Figure 33:
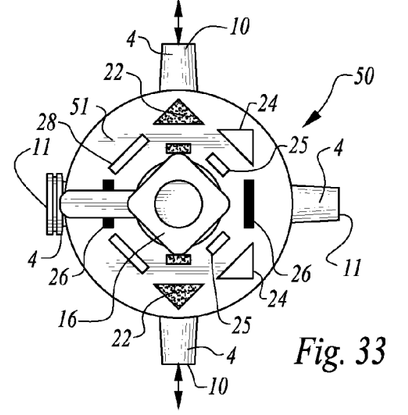
Figure 34:
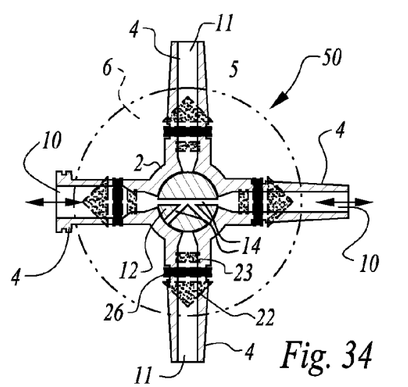
Figure 35:
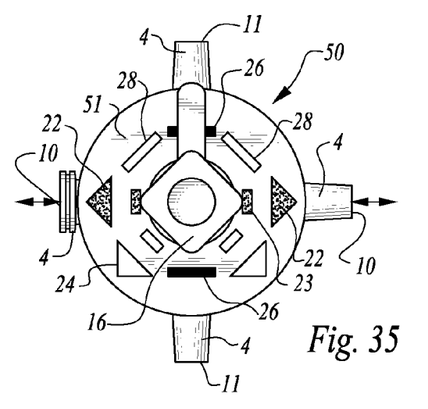

With such a configuration, it can be seen how six different states are provided for the six way stopcock 50, by rotating of the central hub 12 through six different positions, each placed at 45° intervals. A first position is illustrated in FIGS. 32 and 33 which provides two ports 4 opposite each other open (at twelve o'clock and six o'clock positions) and the other two ports opposite each other closed. FIGS. 34 and 35 depict the six way stopcock 50 with the two other ports 4 open (at three o'clock and nine o'clock positions).

Figure 36:
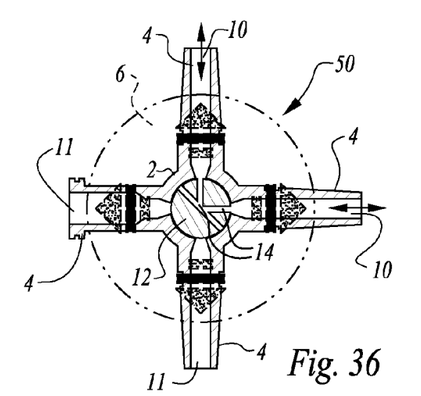
Figure 37:
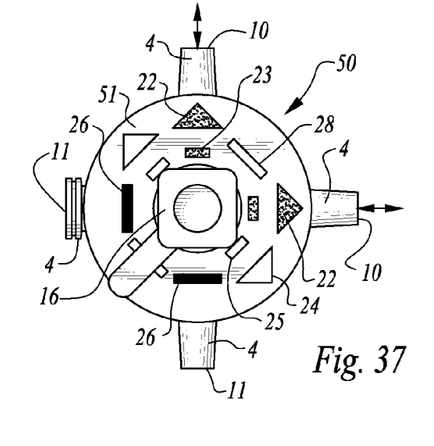
Figure 38:
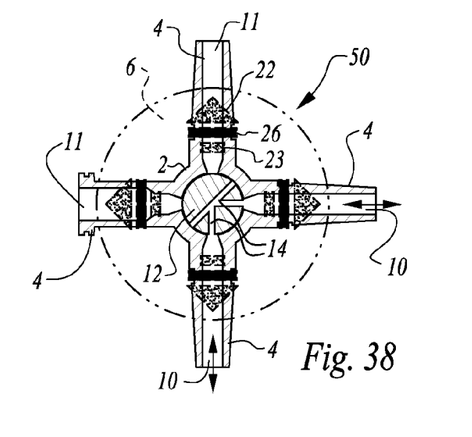
Figure 39:
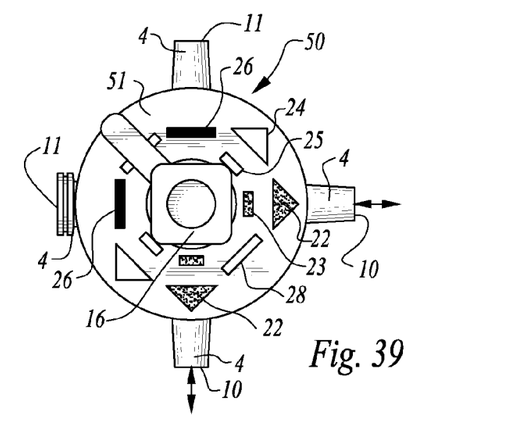
Figure 40:
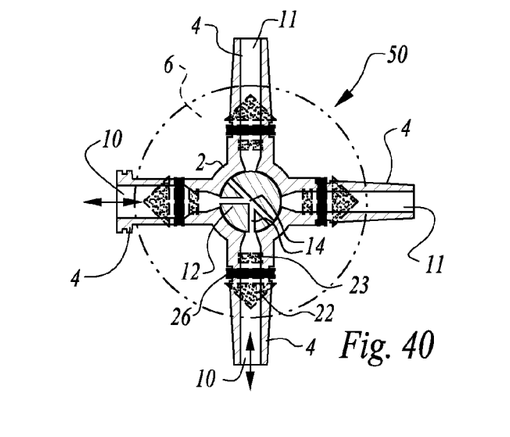
Figure 41:
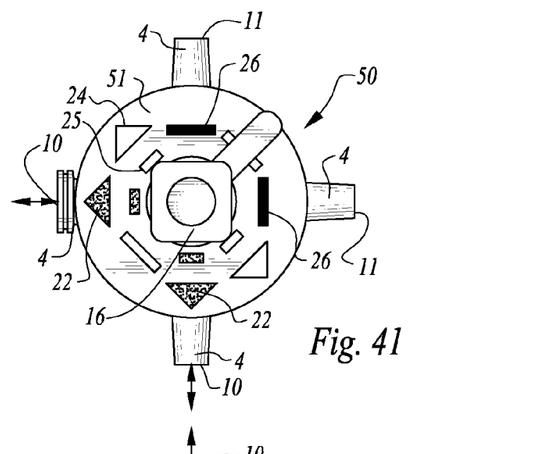
Figure 42:
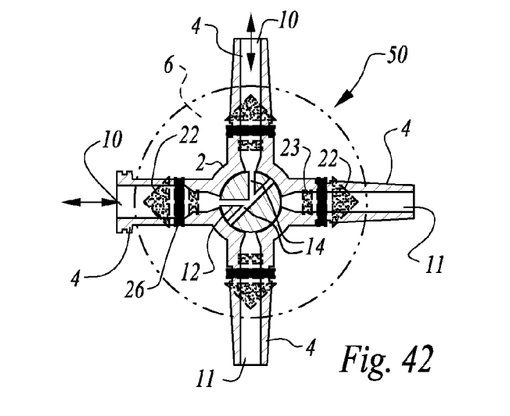
Figure 43:
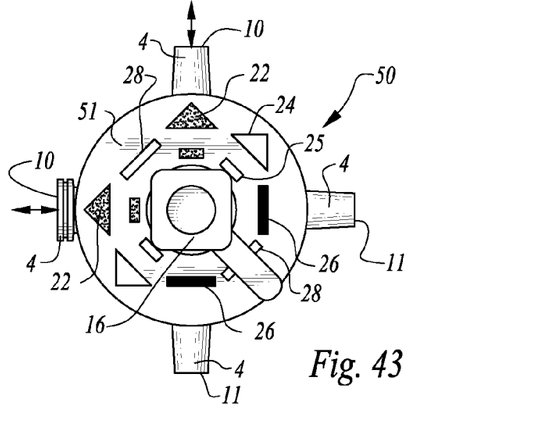

In a third state, the six way stopcock 50 is depicted in FIGS. 36 and 37 with two adjacent ports 4 at a twelve o'clock position and a three o'clock position open, with other positions closed. In FIGS. 38 and 39 the six way stopcock 50 is depicted with ports 4 at the three o'clock and six o'clock position open. In FIGS. 40 and 41 a state of the six way stopcock 50 is depicted where ports 4 at the six o'clock and nine o'clock position are open. In FIGS. 42 and 43 the six way stopcock 50 is shown in a state where ports 4 at the nine o'clock and twelve o'clock position are open. The first plate has additional positive markings 22, 23 at the fourth port 4 location and the second plate 51 has extra positive windows adjacent the additional flow paths in the hub 12.

As with other embodiments, optionally a central control knob 16 can have an axial central fluid path extending through a middle of the central hub 12 and in fluid communication with the flow paths 14 embedded within the central hub 12.

When a user is designing a system which has multiple fluid transport lines, such as medical tubing within a patient treatment environment, the user would initially ascertain the number of different tubes involved and the number of fluid sources and the number of fluid destinations. This total number of fluid sources and destinations is a first factor in determining which stopcock to utilize. Secondarily, the user can ascertain which separate sources or destinations of fluid need to communicate directly together. The user then selects one of the stopcocks having the desired degree of operability and connects medical tubing between the selected stopcock and each of the sources or destinations of fluid. The user may also connect this invention with its flow designating system in series as a manifold for more connectivity if needed, as is done with the prior art. This invention may also include multiple stopcocks molded together as a single unit manifold as is also seen in the prior art.

Thereafter, as the user needs to have fluid conveyed in different ways through the stopcock between sources and destinations for fluids, the user rotates the central hub 12 until the fixed plate 6 and rotating plate 18 (FIGS. 6-13) are aligned to indicate openness and "closedness" of ports 4 corresponding with desired openness and closedness for operation of the overall system. Later, the user can quickly monitor the stopcock to ensure that it is still positioned properly by verifying that the marks on the fixed plate 6 can still be seen and are in the proper positions viewed through the windows of the rotating plate 18. If out of position at all, the user can make appropriate adjustments. When different operational states of the system are required, the central hub 12 is appropriately rotated until the appropriate ports 4 are open or closed to configure the system for the new operational status.

Figures 44, 45, 46:
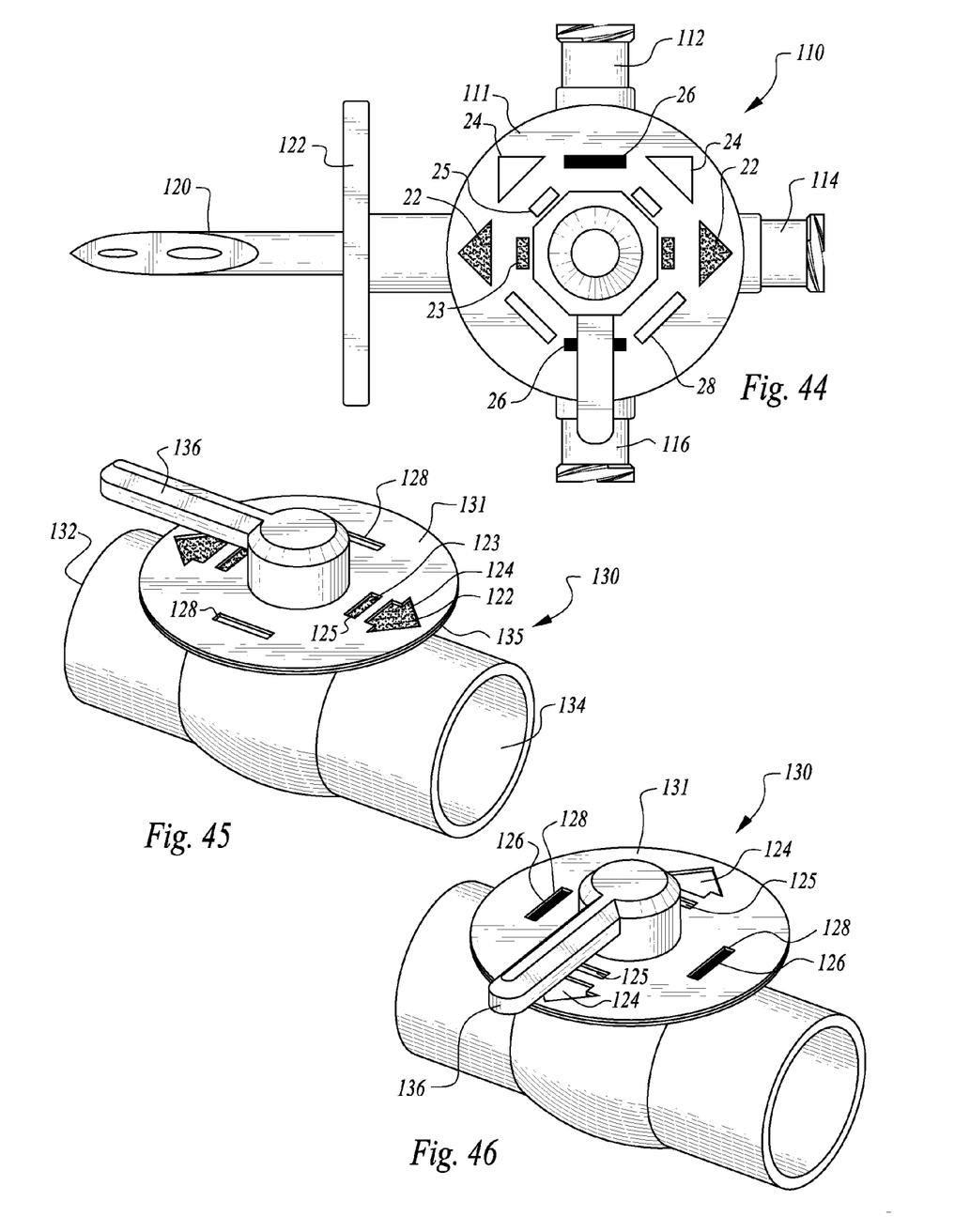
FIG. 44 is a top plan view of a stopcock type valve with one port fixed to a needle-like spike interface, such as for a medication vial.
FIGS. 45-48 are perspective views of two variations of an irrigation or industrial type valve showing how the indicator of this invention can be deployed on valves other than stopcocks.

FIG. 44 depicts a stopcock 110 with an integrated needle-like spike 120 as a further variation of the six way stopcock 50 (FIGS. 32-43). With this stopcock 110 the needle-like spike 120 is built into one of the port locations. Three other ports 112, 114, 116 are fitted with luer lock type couplings in this exemplary embodiment. A shoulder 122 extends radially from a centerline of the needle 120 and although not shown, could employ a feature to hold a bottle of medication. The needle 120 is fitted with a point so that it can conveniently puncture a structure, such as a septum within a bottle of medication, and the shoulder 122 can act as a stop for the assembly. The needle 120 can be fitted with two conduits if desired, such as to allow for both delivery of a liquid and return of gas out of an enclosure. Details of the indicator plate with the stopcock 110 are similar to those described in conjunction with the six way stopcock 50 of FIGS. 32-43.

FIGS. 45 and 46 depict alternative valves 130 which are generally in the form of ball valves, such as those utilized in irrigation or industry and a variety of other liquid or other fluid handling systems. Ports 132, 134 are generally opposite each other in this exemplary embodiment. A control element, such as a valve ball, is coupled to a control handle 136 and is analogous to the central hub of the previously mentioned designs. The control handle 136 can be rotated to open or close the pathway between the ports 132, 134. A pair of indicator plates are provided including a first fixed plate 135 and a second rotating plate 131 which are parallel with each other. Positive markings 122, 123 and negative markings 126 are provided on the first plate 135 at locations aligned with the ports 132, 134. Positive windows 124, 125 are provided aligned with openings in the ball or other control element associated with the handle 136. Negative windows 128 are provided at locations spaced from these openings in the ball or other control element.

As can be seen in FIGS. 45 and 46, the appropriate positive markings 122, 123 or negative markings 126 are visible depending on whether the valve is open or closed. The user always receives a communication, either positive or negative, as to the status of the valve. This indication is correlated to whether the valve is open or closed such as by the shape of the openings in the window or in the shape of the markings. For instance, the open markings can generally appear as arrows and the closed markings can generally appear as blocking walls. Similarly, the color of the markings can be selected to correlate with the status of the valve, such as the color red to indicate closed and the color green to indicate open. By providing multiple positive markings 122, 123 and multiple positive windows 124, 125, a more elongate arrow image can be seen and provide a clear indication that the valve is open. A space between these markings 122, 123 is closed by a bridge between the positive windows 124, 125 to cover the negative marking 126 located between the positive markings 122, 123.

Figure 47:
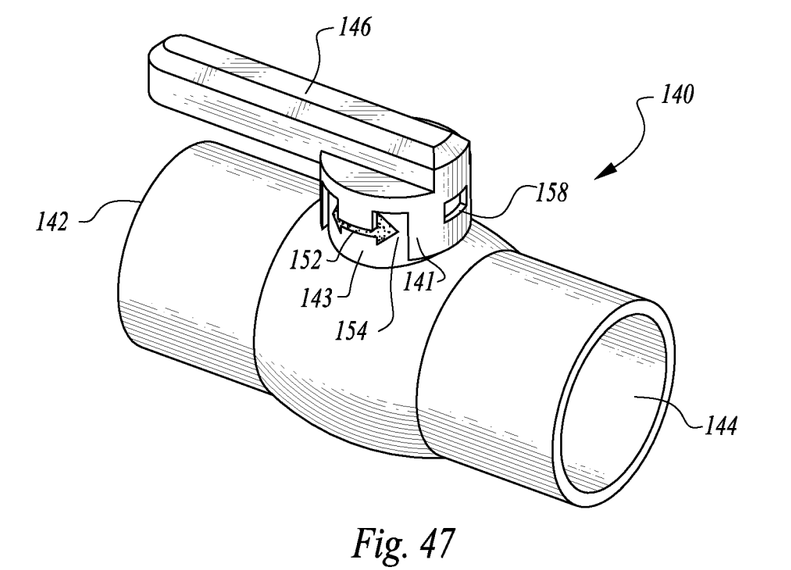
Figure 48:
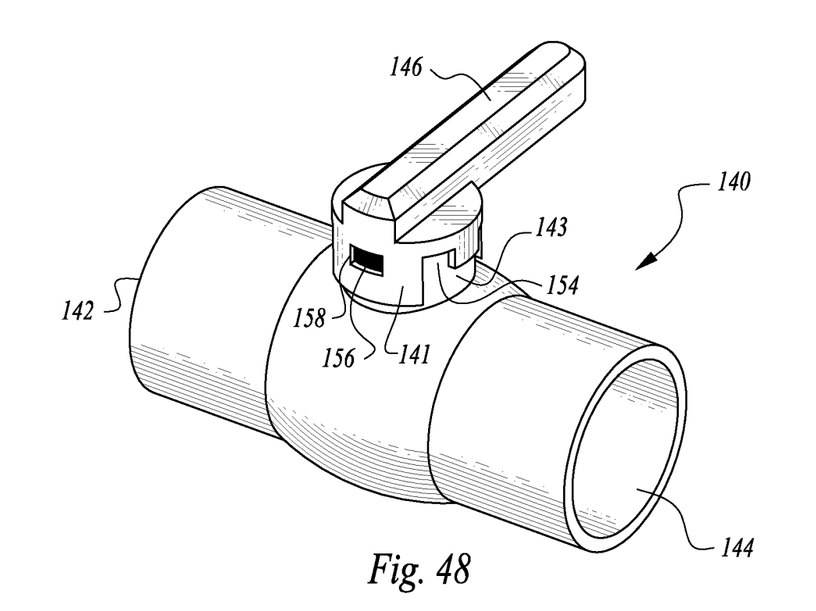

In FIGS. 47 and 48 an alternative valve 140 is disclosed which is configured similar to the valve 130 of FIGS. 45 and 46, except that the indicator structure is uniquely set forth. The valve 140 includes ports 142, 144 at opposite ends and a control arm 146 coupled to a ball or other control element within the valve. The indicator, rather than being in the form of planar plates, is in the form of concentric cylinders. The first fixed indicator portion in the form of a first cylinder is inboard of a second rotating indicator portion in the form of a second cylinder. The first cylinder is fixed to the body of the valve 140 which is also fixed with the ports 142, 144. The second portion is fixed to the control arm 146 and associated ball or other control element within the valve 140. Either a positive marking 152 or a negative marking 156 is visible through either a positive window 154 or a negative window 158 depending on the operational status of the valve, and as depicted in FIGS. 47 and 48. Although only two position valves 130, 140 are shown in FIGS. 45-48, other more complicated valves analogous to the three and four way valves previously demonstrated could also be utilized with these flow demarcating design features.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A stopcock with intuitive positive and negative functional state display identifying flow through the stopcock, the stopcock comprising in combination:
   a valve body;
   at least two fluid pathways joined to said valve body;
   each fluid pathway adapted to route fluid into and out of said valve body;
   a central manifold located within said valve body;
   said central manifold adapted to be rotated relative to said valve body;
   said central manifold having at least one multi-ended flow path therein;
   said central manifold having ends of said at least one multi-ended flow path selectively alignable with various ones of said at least two flow pathways of said valve body;
   a first indicator portion fixed relative to said valve body and having markings thereon including positive markings indicative of open flow and negative markings indicative of closed flow;
   a second indicator portion coupled to said central manifold and overlying said first indicator portion;
   said second indicator portion adapted to rotate when said central manifold rotates;
   said first indicator portion and said second indicator portion interacting to display said positive markings adjacent fluid pathways which are open and said negative markings adjacent fluid pathways which are closed; and
   said first indicator portion and said second indicator portion interacting to not display said positive markings adjacent fluid pathways which are closed and to not display said negative markings adjacent fluid pathways which are open.

2. The stopcock of claim 1 wherein said first indicator portion includes at least one of said positive markings and one of said negative markings adjacent each fluid pathway; and
   said second indicator portion including an object configured to block all of said positive markings of said first indicator except those positive markings which are adjacent fluid pathways of said valve body which are open through said central manifold and block all of said negative markings of said first indicator except those negative markings which are adjacent fluid pathways which are closed.

3. The stopcock of claim 2 wherein said second indicator portion includes a surface with positive windows therein, said positive windows located adjacent to said ends of said at least one multi-ended flow path of said central manifold, such that when said ends of said flow paths of said central manifold are aligned with said fluid pathways of said valve body, said positive markings of said first indicator portion are aligned with said positive windows of said second indicator portion and can be visualized through said surface of said second indicator portion.

4. The stopcock of claim 3 wherein said surface of said second indicator portion includes negative windows therein, said negative widows located adjacent spaces between said ends of said at least one multi-ended flow path of said central manifold, such that when said spaces between said ends of said flow paths of said central manifold are aligned with said fluid pathways of said valve body, said negative markings of said first indicator portion are aligned with said negative windows of said second portion and can be visualized through said surface of said second indicator portion.

5. The stopcock of claim 3 wherein said first indicator portion includes a plate with said markings thereon, said plate located adjacent said surface of said second indicator portion.

6. The stopcock of claim 5 wherein said plate of said first indicator portion and said surface of said second indicator portion are each located on a side of said valve body opposite a side of said valve body having a knob extending therefrom, said knob adapted to be manipulated by a hand of a user to cause said central manifold to rotate relative to said valve body.

7. The stopcock of claim 5 wherein said plate of said first indicator portion and said surface of said second indicator portion are both located on a side of said valve body having a knob coupled to said central manifold, said knob adapted to be manipulated by a user to cause said central manifold to be rotated.

8. The stopcock of claim 1 wherein said positive markings have a distinct appearance from said negative markings.

9. The stopcock of claim 8 wherein said positive markings are a distinct color from said negative markings.

10. The stopcock of claim 1 wherein said central manifold includes an axial flow path extending along a rotational axis of said central manifold at least partially, said axial flow path intersecting at least one of said multi-ended flow paths within said central manifold which extend to said ends of said central manifold, such that an additional flow pathway axially through said stopcock is facilitated.

11. A multi-port valve with positive and negative flow status indicators, comprising in combination:
    a valve body;
    at least two fluid pathways fixed to said valve body;
    said at least two fluid pathways adapted to route fluid into and out of said valve body;
    a central manifold located within said valve body;
    said central manifold adapted to rotate relative to said valve body;
    said central manifold having at least one flow path therein;

said at least one flow path adapted to be selectively aligned with said at least two fluid pathways to control fluid flow through said valve body; and wherein a first indicator portion includes positive markings and negative markings thereon fixed relative to said valve body, a second indicator portion coupled to said central manifold and adapted to rotate when said central manifold rotates, and said first indicator portion and said second indicator portion interacting to display said positive markings indicative of which of said at least two fluid pathways of said valve body are open for flow through said central manifold and to display negative markings indicative of which of said at least two fluid pathways of said valve body are closed to flow through said central manifold.

12. The valve of claim 11 wherein said at least two fluid pathways extend substantially perpendicularly to said rotational axis of said central manifold.

13. The valve of claim 12 wherein said valve body includes at least three fluid pathways, said at least three fluid pathways each oriented in a common plane substantially perpendicular to a rotational axis of said central manifold, two of said at least three fluid pathways oriented substantially 180° away from each other, and one of said fluid pathways oriented substantially perpendicular to each of the other fluid pathways; and wherein said ends of said at least one flow path in said central manifold include at least three ends, two of said ends oriented substantially 180° away from each other and one of said ends oriented substantially 90° away from each of the other of said ends, said at least three ends of said central manifold selectively alignable with various ones of said at least three fluid pathways to selectively couple multiple different ones of said fluid pathways to each other.

14. The valve of claim 11 wherein said second indicator portion includes an object configured to block all of said markings of said first indicator portion except those positive markings which are adjacent fluid pathways of said valve body which are open through said central manifold and to block all of said negative markings of said first indicator portion except those negative markings which are adjacent fluid pathways of said valve body which are closed through said central manifold.

15. The valve of claim 14 wherein said second indicator portion includes a surface with positive and negative windows therein, said positive windows located adjacent ends of said at least one multi-ended flow path of said central manifold, such that when said ends of said flow paths of said central manifold are aligned with said fluid pathways of said valve body, said positive markings of said first indicator portion are aligned with said positive windows of said second indicator portion and can be visualized through said surface of said second indicator portion; and said negative windows located adjacent space between ends of said at least one multi-ended flow path of said central manifold, such that when said spaces between ends of said flow paths of said central manifold are aligned with said fluid pathways of said valve body, said negative markings of said first indicator portion are aligned with said negative windows of said second indicator portion and can be visualized through said surface of said second indicator portion.

16. The valve of claim 11 wherein said positive markings are at least partially arrow shaped and pointing in a direction of flow through the valve when viewed through said positive window.

17. The valve of claim 16 wherein said positive markings are green.

18. The valve of claim 11 wherein said negative markings are elongate in a direction opposed to flow through adjacent said fluid pathways when viewed through said negative windows.

19. The valve of claim 18 wherein said negative markings are red.

20. The valve of claim 11 wherein said positive markings and said negative markings are spaced radially differing distances from a rotational axis of said central manifold and said positive windows and said negative windows are each positioned to be alignable: positive windows with positive markings and negative windows with negative markings.

* * * * *